United States Patent [19]
Sebillote-Arnaud

[11] Patent Number: 5,879,718
[45] Date of Patent: Mar. 9, 1999

[54] COMPOSITION FOR TOPICAL USE IN THE FORM OF A SURFACTANT-FREE OIL-IN-WATER EMULSION CONTAINING A CROSSLINKED AND NEUTRALIZED POLY (2-ACRYLAMIDO-2-METHYLPROPANESULPHONIC ACID) POLYMER

[75] Inventor: Laurence Sebillote-Arnaud, L'Hay Les Roses, France

[73] Assignee: L'Oreal, Paris, France

[21] Appl. No.: 885,595

[22] Filed: Jun. 30, 1997

[30] Foreign Application Priority Data

Jun. 28, 1996 [FR] France .................................. 96 08109

[51] Int. Cl.$^6$ ...................................................... A61K 7/08
[52] U.S. Cl. ............................. 424/705; 424/59; 424/61; 424/70; 424/707; 424/708; 424/401
[58] Field of Search ..................................... 424/401, 701, 424/61, 59, 705, 707, 708; 514/844, 845, 846, 944

[56] References Cited

U.S. PATENT DOCUMENTS 5,114,706   5/1992   Duvel ......................................... 424/70
5,679,328  10/1997   Dupius ................................. 424/70.13

OTHER PUBLICATIONS

Derwent Abstract No. 83–714752 for JP 58–809407 (13 Jun 83).
Derwent Abstract No. 95–354385 for JP 07–241457 (19 Sep 95).

*Primary Examiner*—Jyothsna Venkat
*Attorney, Agent, or Firm*—Finnegan, Henderson, Farabow, Garrett & Dunner, L.L.P.

[57] ABSTRACT

The present application relates to a cosmetic and/or dermatological composition in the form of a surfactant-free oil-in-water emulsion containing at least one crosslinked poly (2-acrylamido-2-methylpropanesulphonic acid) polymer neutralized to at least 90%. The composition contains, distributed randomly:

(a) from 90 to 99.9% by weight of units of formula (1) below:

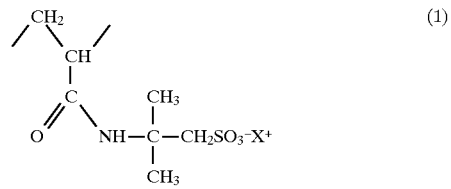

in which $X^+$ denotes a cation or a mixture of cations, it being possible for not more than 10 mol % of the cations $X^+$ to be protons $H^+$; and (b) from 0.01 to 10% by weight of crosslinking units originating from at least one monomer having at least two olefinic double bonds, the weight proportions being defined relative to the total weight of the polymer.

20 Claims, No Drawings

COMPOSITION FOR TOPICAL USE IN THE FORM OF A SURFACTANT-FREE OIL-IN-WATER EMULSION CONTAINING A CROSSLINKED AND NEUTRALIZED POLY (2-ACRYLAMIDO-2-METHYLPROPANESULPHONIC ACID) POLYMER

The present application relates to a cosmetic or dermatological composition in the form of a surfactant-free oil-in-water emulsion containing at least one crosslinked poly (2-acrylamido-2-methylpropanesulphonic acid) polymer neutralized to at least 90%.

For various reasons associated in particular with better comfort during their use, e.g., softness, emollience and the like, the current cosmetic or dermatological compositions are usually in the form of an emulsion of the oil-in-water type, i.e., a support consisting of an aqueous dispersing continuous phase and an oily dispersed discontinuous phase or an emulsion of the water-in-oil type, i.e., a support consisting of a fatty dispersing continuous phase and an aqueous dispersed discontinuous phase. Oil-in-water emulsions are the ones most sought in the cosmetics field since, when they are applied to the skin, they give it a softer, less greasy and lighter feel than do water-in-oil emulsion systems.

The emulsions are generally stabilized with emulsifying surfactants of the oil-in-water type or of the water-in-oil type, which, by virtue of their amphiphilic structure, place themselves at the oilfwater interface and thus stabilize the dispersed droplets. However, these amphiphilic molecules have the drawback of penetrating and irritating the skin, the eyes and the scalp. Moreover, their presence in high concentration leads to anti-cosmetic effects such as a feeling of coarseness or a sticky or tacky feel.

Emulsion formulators are constantly seeking to reduce the content of surfactant in order to improve the harmlessness of these emulsions to the skin, the eyes and the scalp and to improve their cosmetic properties. The main difficulty with which they are generally confronted is to obtain stable emulsions. The aim of the present invention is to produce stable oil-in-water emulsions containing no emulsifying surfactant and having good cosmetic properties.

Poly(2-acrylamido-2-methylpropanesulphonic acid) polymers such as the commercial products COSMEDIA HSP1160 from the company Hoechst and RHEOTIK 8011 from the company Henkel are known in the state of the art. They are used as thickeners or gelling agents in many cosmetic formulations. These polymers do not allow oil-in-water emulsions containing no surfactant to be stabilized.

The inventors have unexpectedly discovered a novel family of poly(2-acrylamido-2-methylpropane- sulphonic acid) polymers which make it possible to produce stable oil-in-water emulsions containing no surfactant.

These polymers also make it possible to prepare oil-in-water emulsions in a wide pH range, the viscosity of which emulsions remains stable over time at room temperature or at higher temperatures. They also make it possible to prepare products, that are homogeneous, non-flowing, non-runny, soft and slippery when applied, and stable on storage.

The present invention relates to a cosmetic or dermatological composition in the form of an oil-in-water emulsion, wherein the composition contains at least one crosslinked poly(2-acrylamido-2-methylpropanesulphonic acid) polymer neutralized to at least 90% and the composition contains no emulsifying surfactant.

The crosslinked and virtually or totally neutralized poly (2-acrylamido-2-methylpropanesulphonic acid) polymers in accordance with the invention are water-soluble or may be swollen in water. They are generally characterized in that they comprise, randomly distributed:

(a) from 90 to 99.9% by weight of units of formula (1) below:

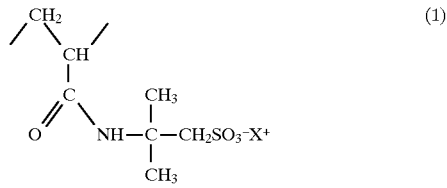

in which $X^+$ denotes a cation or a mixture of cations, it being possible for not more than 10 mol % of the cations $X^+$ to be protons $H^+$; and (b) from 0.01 to 10% by weight of crosslinking units originating from at least one monomer having at least two olefinic double bonds, the weight proportions being defined relative to the total weight of the polymer.

The polymers of the invention preferably contain a number of units of formula (1) in an amount which is sufficiently large to obtain polymer particles whose hydrodynamic volume in aqueous solution has a radius ranging from 10 to 500 nm and whose distribution is homogeneous and unimodal.

The more particularly preferred polymers according to the invention comprise from 98 to 99.5% by weight of units of formula (1) and from 0.2 to 2% by weight of crosslinking units.

$X^+$ represents a cation or a mixture of cations chosen in particular from a proton, an alkali metal cation, a cation equivalent to that of an alkaline-earth metal or the ammonium ion. More particularly, 90 to 100 mol % of the cations are $NH_4^+$ cations and 0 to 10 mol % are protons ($H^+$).

The crosslinking monomers having at least two olefinic double bonds are selected, for example, from dipropylene glycol diallyl ether, polyglycol diallyl ether, triethylene glycol divinyl ether, hydroquinone diallyl ether, tetrallyloxyethanoyl or other polyfunctional allyl or vinyl ether alcohols, tetraethylene glycol diacrylate, triallylamine, trimethylolpropane diallyl ether, methylenebisacrylamide or divinylbenzene.

The crosslinking monomers having at least two olefinic double bonds are more particularly selected from those corresponding to formula (2) below:

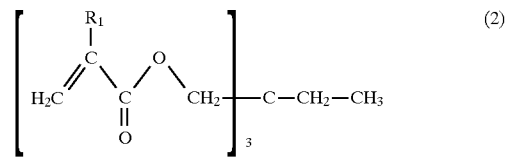

in which $R_1$ denotes a hydrogen atom or a $C_{1-4}$ alkyl. The crosslinking monomer is more particularly methyl (trimethylolpropane triacrylate).

The reaction to polymerize the polymers of the invention produces not only linear chains but also branched or crosslinked polymer molecules. These molecules may be characterized in particular by their Theological behavior in water, but more particularly by their dynamic light scattering.

For the characterization of the molecules by their dynamic light scattering, the distribution of the hydrodynamic volume of the polymer structures is measured. The macromolecules dissolved in the water are flexible and surrounded by a salvation sheath formed of water molecules. With charged polymers such as those of the invention, the size of the molecules depends on the amount of salt in the water. In polar solvents, the uniform charge along the main chain of the polymer leads to a large expansion of the polymer chain. Increasing the amount of salt increases the amount of electrolyte in the solvent and shields the uniform charges of the polymer. In addition to the molecules transported in the solvation sheath, solvent molecules are bound in the cavities of the polymer. In this case, the solvent molecules form part of the macromolecules in solution and travel at the same average speed. Thus, the hydrodynamic volume describes the linear size of the macromolecule and of its salvation molecules.

The hydrodynamic volume $v_h$ is determined by the following formula:

$$V_h = M/N_A \times (V_2 + dV_1)$$

with:

M denoting the mass in grams of the undissolved macromolecule;

$N_A$ denoting Avogadro's number;

$V_1$ denoting the specific volume of the solvent;

$V_2$ denoting the specific volume of the macromolecule; and d denoting the mass in grams of the solvent which is associated with 1 gram of undissolved macromolecule.

If the hydrodynamic particle is spherical, it is then easy to calculate the hydrodynamic radius from the hydrodynamic volume, by the formula:

$$V_h = 4\pi R^3/3$$

with R denoting the dynamic radius.

Cases where the hydrodynamic particles are perfect spheres are extremely rare. Most synthetic polymers involve compacted structures or ellipsoids of high eccentricity. In this case, the radius is determined on a sphere which is equivalent, from a frictional point of view, to the shape of the particle considered.

As a general rule, work is carried out on molecular weight distributions and thus on radius distributions and on hydrodynamic volume distributions. For the polydispersed systems, the distribution of the scattering coefficients must be calculated. From this distribution, the results relating to the radial distribution and to the hydrodynamic volume distribution are deduced.

The hydrodynamic volumes of the polymers of the invention are determined in particular by dynamic light scattering from the scattering coefficients D according to Stokes-Einstein of formula: $D = kT/6\pi\eta R$ where k is the Boltzmann constant, T the absolute temperature in degrees Kelvin, $\eta$ is the viscosity of the solvent (water) and R is the hydrodynamic radius.

These scattering coefficients D are measured according to the method for characterizing a mixture of polymers by laser scattering, described in the following references:

(1) Pecora, R.; Dynamic Light Scattering; Plenum Press, New York, 1976;

(2) Chu, B.; Dynamic Light Scattering; Academic Press, New York, 1994;

(3) Schmitz, K. S.; Introduction to Dynamic Light Scattering; Academic Press, New York, 1990;

(4) Provincher S. W.; Comp. Phys., 27,213, 1982;

(5) Provincher S. W.; Comp. Phys., 27, 229,1982;

(6) ALV Laservertriebgesellschaft mbH, Robert Bosch Str. 47, D-63225 Langen, Germany;

(7) ELS-Reinheimer Strasse 11, D-64846 Gross-Zimmern, Germany;

(8) CHI WU et al., Macromolecules, 1995, 28, 4914–4919.

The polymers which are particularly preferred are those having a viscosity, measured with a Brookfield viscometer, rotor 4, at a spinspeed of 100 revolutions/minute in an aqueous solution at a concentration of 2% and at 25° C., of greater than or equal to 1000 cps, preferably ranging from 5000 to 40,000 cPs and more preferably ranging from 6500 to 35,000 cPs.

The crosslinked poly(2-acrylamido-2-methylpropanesulphonic acid) polymer of the invention may be obtained according to the preparation process comprising the following steps:

(a) the 2-acrylamido-2-methylpropanesulphonic acid monomer in free form is dispersed or dissolved in a solution of tert-butanol or of water and tert-butanol;

(b) the solution or dispersion of monomer obtained in (a) is neutralized with one or more inorganic or organic bases, preferably aqueous ammonia $NH_3$, in an amount which makes it possible to obtain a degree of neutralization of the sulphonic acid functions of the polymer ranging from 90 to 100%;

(c) the crosslinking monomer or monomers is (are) added to the solution or dispersion obtained in (b); and (d) a standard radical polymerization is carried out in the presence of free-radical initiators, at a temperature ranging from 10° to 150° C., the polymer precipitating in the solution or dispersion based on tert-butanol.

Another subject of the invention consists of cosmetic or dermatological compositions containing, in a cosmetically acceptable medium, at least one crosslinked poly(2-acrylamido-2-methylpropanesulphonic acid) polymer which is neutralized to at least 90% as described above.

The at least one crosslinked, virtually or totally neutralized poly(2-acrylamido-2-methylpropanesulphonic acid) polymer is present in the cosmetic or dermatological compositions of the invention in concentrations preferably ranging from 0.01 to 20% by weight with respect to the total weight of the composition and more preferably from 0.1 to 10% by weight.

The compositions of the invention also contain a cosmetically or dermatologically acceptable medium, i.e., a medium which is compatible with any keratin substance, such as the skin, the nails, the mucous membranes and the hair or any other area of body skin.

The compositions preferably contain a cosmetically or dermatologically acceptable aqueous medium. They have a pH which may preferably range from 1 to 13 and more preferably from 2 to 12.

The compositions according to the invention may contain, in addition to water, one or more cosmetically or dermatologically acceptable organic solvents. The dermatologically acceptable organic solvents have acceptable tolerance, toxicology and feel.

The organic solvents may represent from 5% to 98% of the total weight of the composition. They may be selected from hydrophilic organic solvents, lipophilic organic solvents, amphiphilic solvents and mixtures thereof.

Among the hydrophilic organic solvents, mention may be made, for example, of linear or branched lower monoalcohols having from 1 to 8 carbon atoms, such as ethanol, propanol, butanol, isopropanol and isobutanol; polyethylene glycols having from 6 to 80 ethylene oxides; polyols such as propylene glycol, isoprene glycol, butylene glycol, glycerol and sorbitol; mono- or dialkyl isosorbides in which the alkyl groups have from 1 to 5 carbon atoms, such as dimethyl isosorbide; glycol ethers such as diethylene glycol monomethyl or monoethyl ether and propylene glycol ethers such as dipropylene glycol methyl ether.

Among the amphiphilic organic solvents, mention may be made, for example, of polyols such as polypropylene glycol (PPG) derivatives, for instance polypropylene glycol esters of fatty acid and PPG ethers of fatty alcohol, for instance PPG-36 oleate, PPG-23 oleyl ether. Lipophilic organic solvents which may be mentioned, for example, are fatty esters such as diisopropyl adipate, dioctyl adipate and alkyl benzoates.

In order for the cosmetic or dermatological compositions of the invention to be more pleasant to use, i.e., softer on application, more nourishing, and more emollient, it is possible to add a fatty phase to the medium of these compositions.

The fatty phase of the compositions according to the invention preferably represents from 0% to 50% of the total weight of the composition. This fatty phase may contain one or more oils preferably selected from:

volatile or nonvolatile, linear, branched or cyclic, organically modified or otherwise, water-soluble or liposoluble silicones;

mineral oils such as liquid paraffin and liquid petrolatum;

oils of animal origin such as perhydrosqualene;

oils of plant origin such as sweet almond oil, avocado oil, castor oil, olive oil, jojoba oil, sesame oil, groundnut oil, macadamia oil, blackcurrant pip oil, rapeseed oil and coconut oil;

synthetic oils such as purcellin oil and isoparaffins;

fluoro oils and perfluoro oils; and fatty acid esters such as purcellin oil.

It may also contain one or more fatty alcohols, fatty acids such as stearic acid or waxes such as paraffin, polyethylene wax, carnauba wax, and beeswax as fatty substance.

All the compositions of the invention may contain adjuvants that are common in the cosmetic and dermatological fields, and other standard gelling agents or thickeners; polymers; hydrating agents; emollients; sunscreens; hydrophilic or lipophilic active agents such as ceramides; anti-free-radical agents; insect repellants; slimming agents; bactericides; sequestering agents; anti-dandruff agents; antioxidants; preserving agents; basifying or acidifying agents; fragrances; fillers; and dyestuffs. The amounts of these various adjuvants are those conventionally used in the fields considered.

Obviously, a person skilled in the art will take care to select the optional compound or compounds to be added to the composition according to the invention such that the advantageous properties intrinsically associated with the composition in accordance with the invention are not, or are not substantially, adversely affected by the addition envisaged.

The compositions according to the invention may be in the form of serum, milk, creams that are more or less creamy, or paste. These compositions are prepared according to the usual methods.

The compositions according to the invention may be used for the preparation of or as rinse-out hair products or as leave-in hair products in particular to care for and condition the hair.

The compositions of the invention may also be used for the preparation of or as a product to care for the skin, the hair, the scalp, the eyelashes, the eyebrows, the nails or the mucous membranes, such as protective, treating or care creams for the face, for the hands or for the body, protective or care body milks, lotions, gels or foams to care for the skin and the mucous membranes or to cleanse the skin.

The compositions of the invention may also be used for the preparation of or as an antisun product.

The compositions may be used for the preparation of or as make-up products such as face creams and foundations.

Another subject of the invention is a process for the cosmetic, non-therapeutic treatment of a keratinous support such as the skin, the scalp, the hair, the eyelashes, the eyebrows, the nails or the mucous membranes, characterized in that a composition as defined above is applied to the keratinous support according to the usual technique for using this composition. For example, the process may encompass application of creams, gels, sera, lotions or milks to the skin, the scalp or the mucous membranes.

The examples which follow illustrate the invention without being limiting in nature.

PREPARATION EXAMPLE A 2006.2 g of tert-butanol were introduced into a 5-liter round-bottomed flask fitted with a stirrer, a reflux condenser, a thermometer and a device for conveying nitrogen and aqueous ammonia, after which 340.0 g of 2-acrylamido-2-methylpropanesulphonic acid was introduced and was dispersed in the solution with vigorous stirring. After 30 minutes, aqueous ammonia was added via the upper conduit of the flask and the reaction mixture was maintained at room temperature for 30 minutes until a pH of about 6–6.5 was obtained. A 32.0 g solution of trimethylolpropane triacrylate at a concentration of 25% in tert-butanol was then introduced and the reaction medium was heated to 60° C. while at the same time being made inert by the addition of nitrogen into the flask. Once this temperature was reached, dilauroyl peroxide was added. The reaction started immediately, and this was reflected in a temperature rise and precipitation of the polymerizate. After 15 minutes of polymerization, a stream of nitrogen was introduced. After 30 minutes of adding the initiator, the temperature of the reaction medium reached a maximum of 65°–70° C. Thirty minutes after this temperature had been reached, the mixture was heated to reflux and maintained under these conditions for 2 hours. It was observed that a thick paste formed during the reaction.

The mixture was cooled to room temperature and the product obtained was filtered off. The paste recovered was then dried under vacuum at 60°–70° C. for 24 hours. A 391 g amount of crosslinked and neutralized poly(2-acrylamido-2-methylpropanesulphonic acid) was obtained, having a viscosity, measured with a Brookfield viscometer, rotor 4, at a spinspeed of 100 revolutions/minute in an aqueous solution at a concentration of 2% and at 25° C., ranging from 15,000 cps to 35,000 cps. The viscosity of the polymer was chosen and controlled according to standard means as a function of the cosmetic application envisaged.

The hydrodynamic radius of the polymer obtained in an aqueous solution, determined by dynamic light scattering, was 440 nm.

PREPARATION EXAMPLE B

About 2006.2 g of tert-butanol was introduced into a 5-litre round-bottomed flask fitted with a stirrer, a reflux condenser, a thermometer and a device for conveying nitrogen and aqueous ammonia, after which 340.0 g of 2-acrylamido-2-methylpropanesulphonic acid was introduced and was dispersed in the solution with vigorous stirring. After 30 minutes, aqueous ammonia was added via the upper conduit of the flask and the reaction mixture was maintained at room temperature for 30 minutes until a pH of about 6–6.5 was obtained. A 19.2 g solution of trimethylolpropane triacrylate at a concentration of 25% in tert-butanol was then introduced and the reaction medium was heated to 60° C. while at the same time being made inert by addition of nitrogen into the flask. Once this temperature was reached, dilauroyl peroxide was added. The reaction started immediately, and this was reflected in a temperature rise and precipitation of the polymerizate. After 15 minutes of polymerization, a stream of nitrogen was introduced. After 30 minutes of adding the initiator, the temperature of the reaction mixture reached a maximum of 65°–70° C. Thirty minutes after this temperature had been reached, the mixture was heated to reflux and maintained under these conditions for 2 hours. It was observed that a thick paste formed during the reaction.

The mixture was cooled to room temperature and the product obtained was filtered off. The paste recovered was then dried under vacuum at 60°–70° C. for 24 hours. A 391 g amount of crosslinked and neutralized poly(2-acrylamido-2-methylpropanesulphonic acid) was obtained, having a viscosity, measured with a Brookfield viscometer, rotor 4, at a spinspeed of 100 revolutions/minute in an aqueous solution at a concentration of 2% and at 25° C., of about 7000 cps.

The hydrodynamic radius of the polymer obtained in an aqueous solution, determined by dynamic light scattering, was 160 nm.

COMPARATIVE TESTS

The macroscopic appearance and the microscopic appearance of oil-in-water emulsions (1) according to the invention, containing no surfactant, which were thickened with a poly(2-acrylamido-2-methylpropanesulphonic acid) polymer which was crosslinked and neutralized with aqueous ammonia, prepared according to the process of Preparation Example A, with a viscosity of about 16,000 cps in an aqueous solution at a concentration of 2% and at 25° C., were studied.

These compositions were compared with oil-in-water emulsions (2) according to the prior art, containing a non-crosslinked poly(2-acrylamido-2-methylpropanesulphonic acid) polymer as thickener, such as the commercial product COSMEDIA HSP1160 sold by Henkel.

Compositions (1) and (2) have the following formulations:

COMPOSITION (1)

| Fatty phase | |
|---|---|
| Sweet almond oil | 7.0 g |
| Cyclomethicone | 5.0 g |
| Aqueous phase | |
| Crosslinked poly(2-acrylamido-2-methyl-propanesulphonic acid) neutralized with aqueous ammonia, prepared according to the process of Preparation Example A, with a viscosity of about 16,000 cps in aqueous solution at a concentration of 2% and at 25° C. | 0.5–2 g AM |
| Distilled water qs | 100 g |
| pH 2 to 7 | |

COMPOSITION (2)

| Fatty phase | |
|---|---|
| Sweet almond oil | 7.0 g |
| Cyclomethicone | 5.0 g |
| Aqueous phase | |
| Non-crosslinked poly(2-acrylamido-2-methyl-propanesulphonic acid) neutralized with triethanolamine, solid under the name COSMEDIA HSP1160 | 0.5–11 g AM |
| Distilled water qs | 100 g |
| pH 2 to 7 | |

Gels or creams which were relatively thickened, stable, homogeneous, non-sticky and non-runny were obtained with the compositions (1). Stable, fine, uniform and homogeneous dispersions of the oil droplets were observed by microscope.

Fluid, unstable, heterogeneous, tacky, runny and sticky gels were obtained with the compositions (2), even at high concentrations of thickening polymer (11% active material). Unstable, coarse, non-uniform and heterogeneous dispersions of the oil droplets were observed by microscope.

EXAMPLE 1

Moisturizing cream

| Fatty phase | |
|---|---|
| Sweet almond oil | 7.0 g |
| Cyclomethicone | 5.0 g |
| Aqueous phase | |
| Crosslinked poly(2-acrylamido-2-methyl-propanesulphonic acid) neutralized with aqueous ammonia, prepared according to the process of Preparation Example A, with a viscosity of about 16,000 cps in aqueous solution at a concentration of 2% and at 25° C. | 1.5 g AM |
| Glycerol | 7.0 g |
| Preserving agent qs | |
| Distilled water qs | 100 g |
| pH 6 | |

A homogeneous, shiny, white gelled cream was obtained.

EXAMPLE 2

Mild acidic desquamating cream

| Fatty phase | |
|---|---|
| Sweet almond oil | 10.0 g |
| Aqueous phase | |
| Crosslinked poly(2-acrylamido-2-methyl-propanesulphonic acid) neutralized with aqueous ammonia, prepared according to the process of Preparation Example A, with a viscosity of about 16,000 cps in aqueous solution at a concentration of 2% and at 25° C. | 2 g AM |
| Malic acid | 1.0 g |
| Tartaric acid | 1.0 g |
| Preserving agent qs | |
| Distilled water qs | 100 g |
| pH 3.5 | |

A homogeneous, shiny, thick white cream was obtained.

EXAMPLE 3
Refreshing fluid for greasy skins

| Fatty phase | |
|---|---|
| Volatile silicone | 5.0 g |
| Aqueous phase | |
| Crosslinked poly(2-acrylamido-2-methyl-propanesulphonic acid) neutralized with aqueous ammonia, prepared according to the process of Preparation A, with a viscosity of about 16,000 cps, in an aqueous solution at a concentration of 2% and at 25° C. | 0.5 g AM |
| Ethyl alcohol | 20.0 g |
| Preserving agent qs | |
| Distilled water qs | 100 g |
| pH 6 | |

A homogeneous, stable, translucent fluid was obtained.

EXAMPLE 4
Fluid acidic depigmenting emulsion

| Fatty phase | |
|---|---|
| Avocado oil | 8.0 g |
| Aqueous phase | |
| Crosslinked poly(2-acrylamido-2-methyl-propanesulphonic acid) neutralized with aqueous ammonia, prepared according to the process of Preparation. Example A, with a viscosity of about 16,000 cps in an aqueous solution at a concentration of 2% and at 25° C. | 0.7 g AM |
| Kojic acid | 1.0 g |
| 3,3'-Terephthalidine-10,10'-dicamphor-sulphonic acid | 0.7 g |
| Triethanolamine qs | |
| Preserving agent qs | |
| Distilled water qs | 100 g |
| pH 3 | |

A homogeneous, stable fluid of emulsified appearance was obtained.

EXAMPLE 5
Relaxing gel for tired legs

| Fatty phase | |
|---|---|
| Liquid fraction of karite butter | 3 g |
| Cyclomethicone | 3 g |
| Aqueous phase | |
| Crosslinked poly(2-acrylamido-2-methyl-propanesulphonic acid) neutralized with aqueous ammonia, prepared according to the process of Preparation Example B, with a viscosity of about 7000 cps in an aqueous solution at a concentration of 2% and at 25° C. | 1.5 g AM |
| 96° ethyl alcohol in water | 20 g |
| Glycerol | 3 g |
| Propylene glycol | 3 g |
| Menthol | 0.3 g |
| Camphor | 0.2 g |
| Demineralized water qs | 100 g |
| pH 5 | |

A smooth, homogeneous, shiny white gel was obtained.

What is claimed is:

1. A cosmetic or dermatological composition in the form of an oil-in-water emulsion, wherein the composition contains at least one crosslinked poly(2-acrylamido-2-methylpropanesulphonic acid) polymer neutralized to at least 90% and wherein the composition contains no surfactant, and further wherein said at least one crosslinked poly(2-acrylamido-2-methylpropanesulphonic acid) polymer comprises, randomly distributed:

a) from 90 to 99.9% by weight, relative to the weight of said at least one crosslinked polymer, of units of formula (1) below:

$$\begin{array}{c} CH_2 \\ \diagdown \\ CH \\ | \\ C \qquad CH_3 \\ \diagup\diagdown \qquad | \\ O \qquad NH-C-CH_2SO_3^-X^+ \\ | \\ CH_3 \end{array} \quad (1)$$

in which $X^+$ denotes a cation or a mixture of cations, it being possible for not more than 10 mol % of the cations $X^+$ to be protons $H^+$; and (b) from 0.01 to 10% by weight, relative to the weight of said at least one crosslinked polymer, of crosslinking units originating from at least one monomer having at least two olefinic double bonds, wherein said at least one monomer is dipropylene glycol diallyl ether, polyglycol diallyl ether, triethylene glycol divinyl ether, hydroquinone diallyl ether, tetraethylene glycol diacrylate, triallylamine, trimethylolpropane diallyl ether, or a compound corresponding to formula (2) below:

$$\left[ \begin{array}{c} R_1 \\ | \\ C \qquad O \\ \diagup\diagdown\diagup \\ H_2C \qquad C \qquad CH_2 \\ || \\ O \end{array} \right]_3 -C-CH_2-CH_3 \quad (2)$$

in which $R_1$ denotes a hydrogen atom or a $C_1$–$C_4$ alkyl.

2. A composition according to claim 1, wherein said at least one crosslinked poly(2-acrylamido-2-methylpropanesulphonic acid) polymer neutralized to at least 90%, contains a number of units of formula (1) in an amount which is sufficiently large to obtain polymer particles whose hydrodynamic volume in aqueous solution has a radius ranging from 10 to 500 nm and whose distribution is homogeneous and unimodal.

3. A composition according to claim 1, wherein said at least one crosslinked poly(2-acrylamido-2-methylpropanesulphonic acid) polymer contains from 98 to 99.5% by weight of units of formula (1) and from 0.2 to 2% by weight of crosslinking units.

4. A composition according to claim 1, wherein, in formula (1), the cation $X^+$ is $NH_4^+$.

5. A composition according to claim 1, wherein said at least one crosslinked poly(2-acrylamido-2-methylpropanesulphonic acid) polymer is crosslinked with trimethylolpropane triacrylate.

6. A composition according to claim 1, wherein the polymers of formula (1), when present in an aqueous solution at a concentration of 2%, have a viscosity, measured with a Brookfield viscometer, rotor 4, speed 100 revolutions/minute at 25° C., of greater than or equal to 1000 cps.

7. A composition according to claim 6, wherein the polymers of formula (1) have a viscosity ranging from 5000 to 40,000 cps. and more particularly from 6500 to 35,000 cps.

8. A composition according to claim 7, wherein the polymers of formula (1) have a viscosity ranging from 6500 to 35,000 cps.

9. A composition according to claim 1, wherein said at least one crosslinked poly(2-acrylamido-2-methylpropanesulphonic acid) polymer is present in concentrations ranging from 0.01 to 20% by weight relative to the total weight of the composition.

10. A composition according to claim 9, wherein said at least one crosslinked poly(2-acrylamido-2-methylpropanesulphonic acid) polymer is present in concentrations ranging from 0.1 to 10% by weight relative to the total weight of the composition.

11. A composition according to claim 1, wherein said composition has a pH ranging from 1 to 13.

12. A composition according to claim 1, wherein said composition also contains at least one organic solvent selected from the group consisting of hydrophilic organic solvents, lipophilic organic solvents, amphiphilic solvents and mixtures thereof.

13. A composition according to claim 12, wherein said at least one organic solvent is a mono- or polyfunctional alcohol, an oxyethylenated polyethylene glycol, a propylene glycol ester, a sorbitol, a di-alkyl isosorbide, a glycol ether, a propylene glycol ether, or a fatty ester.

14. A composition according to claim 12, wherein said at least one organic solvent represents from 5% to 98% of the total weight of the composition.

15. A composition according to claim 1, wherein said composition additionally comprises at least one fatty phase.

16. A composition according to claim 15, wherein said at least one fatty phase represents up to 50% of the total weight of the composition.

17. A composition according to claim 1, wherein said composition additionally contains at least one additive selected from the group consisting of standard aqueous or lipophilic gelling agents or thickeners; hydrophilic or lipophilic active agents; preserving agents; antioxidants; fragrances; hydrating agents; emollients; sequestering agents; surfactants; polymers; basifying or acidifying agents; fillers; anti-free-radical agents; ceramides; sunscreens; insect repellants; slimming agents; dyestuffs; bactericides; and anti-dandruff agents.

18. A method for caring or for conditioning of the hairstyle or shaping the hair, said method comprising applying an effective amount of a composition according to claim 1 to the hair as a rinse-out or leave-in hair product.

19. A process for the non-therapeutic cosmetic treatment of skin, scalp, hair, eyelashes, eyebrows, nails or mucous membranes, wherein an effective amount of a composition according to claim 1 is applied on said skin, scalp, hair, eyelashes, eyebrows, nails or mucous membranes.

20. A process according to claim 19, wherein said composition is a make-up product, or an anti-sun product.

* * * * *

UNITED STATES PATENT AND TRADEMARK OFFICE
CERTIFICATE OF CORRECTION

PATENT NO. : 5,879,718
DATED : March 9, 1999
INVENTOR(S) : Laurence SEBILLOTTE-ARNAUD It is certified that error appears in the above-identified patent and that said Letters Patent is hereby corrected as shown below:

On the title page, item [19]:

Change "Sebillote-Arnaud" to --Sebillotte-Arnaud et al.--.

In the "Inventor" section, change "Inventor: Laurence Sebillote-Arnaud" to --Inventors: Laurence Sebillotte-Arnaud--;
line 2, after "France" insert --; and Raluca Lorant, Thiais, France--.

IN THE CLAIMS:

Claim 1, col. 10, line 25, change "polyg-:" to --poly---;

line 26, change "lycol" to --glycol--.

Claim 2, col. 10, line 41, after "90%" delete ",".

Signed and Sealed this

Sixth Day of July, 1999

Attest:

Attesting Officer

Q. TODD DICKINSON

Acting Commissioner of Patents and Trademarks